United States Patent
Norman, Jr.

(10) Patent No.: US 6,658,431 B1
(45) Date of Patent: Dec. 2, 2003

(54) METHOD AND APPARATUS FOR DIRECTING INTERNET USERS TO HEALTH CARE INFORMATION SUCH AS NAMES OF HEALTH CARE PROVIDERS

(75) Inventor: James G. Norman, Jr., Tampa, FL (US)

(73) Assignee: Intermap Systems, Inc., Berkeley, CA (US)

( * ) Notice: Subject to any disclaimer, the term of this patent is extended or adjusted under 35 U.S.C. 154(b) by 72 days.

(21) Appl. No.: 09/655,563

(22) Filed: Sep. 6, 2000

(51) Int. Cl.[7] .............................................. G06F 17/30
(52) U.S. Cl. ...................... 707/104.1; 707/10; 705/2; 705/3
(58) Field of Search .................... 707/1, 5, 10, 102, 707/104.1; 705/2, 3; 345/762, 763; 600/300

(56) References Cited

U.S. PATENT DOCUMENTS

| | | | |
|---|---|---|---|
| 5,964,700 A | * 10/1999 | Tallman et al. | 600/300 |
| 6,302,844 B1 | * 10/2001 | Walker et al. | 600/300 |
| 6,381,576 B1 | * 4/2002 | Gilbert | 600/300 |
| 6,482,156 B2 | * 11/2002 | Iliff | 600/300 |
| 6,533,724 B2 | * 3/2003 | McNair | 600/300 |

* cited by examiner

Primary Examiner—Diane D. Mizrahi
(74) Attorney, Agent, or Firm—Thompson Coburn LLP

(57) ABSTRACT

A method including storing content in a computer database, the content having a plurality of components. The method further comprises associating each of at least some of the content components with at least one of a plurality of codes (such as ICD or CPT codes) in a manner so that each of the plurality of codes employed has at least one of the content components associated therewith, and providing a retrieval system accessible by a user using the Internet. The retrieval system is adapted to retrieve the content components associated with any one of the codes upon receiving a signal sent by the user. The signal corresponds to said any one of the codes. The content components associated with said any one of codes are sent to the user upon receiving the signal.

17 Claims, 2 Drawing Sheets

METHOD AND APPARATUS FOR DIRECTING INTERNET USERS TO HEALTH CARE INFORMATION SUCH AS NAMES OF HEALTH CARE PROVIDERS

BACKGROUND OF THE INVENTION

This invention relates to methods and apparatus for directing Internet users to health care information.

The Internet is a rich source of information on a wide variety of subjects such as medicine. The field of medicine, however, is vast and technically complex, and involves many terms of art which are not in the vocabulary of a typical Internet user. An Internet user who happens to locate health care information relevant to a particular ailment or concern might desire to locate a health care provider for treatment or advice. If the Internet user knows the type of health care provider or type of specialty best suited for providing such treatment or advise, he/she might be able to locate a qualified health care provider via a telephone book or insurance list of providers. In many cases, however, the user will not know the type of specialty best suited for his/her ailment or concern and will not know how to locate a specialist. Also, sub-specialists often exist within specialties. For example, general surgeons include vascular surgeons, colon and rectal surgeons, endocrine surgeons, breast surgeons, oncologic surgeons, etc. Sub-specialties are generally not listed in telephone books or insurance lists of providers and are typically not indexed or followed. Further, some sub-specialties are so specific that relatively few such sub-specialists exist in the entire U.S. or world and may be geographically remote from the Internet user. As such, such sub-specialist could not be located via a local telephone book or insurance list of providers. This problem causes all sub-specialists to be listed and indexed by their general classification, and therefore patients cannot find the correct specialist.

Presently, some web sites facilitate searching names of physicians by specialty for a particular geographic location. However, the areas of specialty are somewhat broad, and no provision is available for refining the search by sub-specialty. Also, no provision is made for locating a physician based on an ailment, condition, or desired procedure. This is especially troublesome since patients nearly always need a specialist because of the need for a very specific procedure or therapeutic intervention.

SUMMARY OF THE INVENTION

Among the features and advantages of the present invention may be noted the provision of an improved method for providing specific and relevant health care information to Internet users; the provision of such a method for directing Internet users to the names of health care providers for treating specific ailments or conditions regardless of whether the users know what type of specialist treats such ailments or conditions; the provision of such a method for directing Internet users to pertinent and specific content, such as the names of health care providers, relating to health care information with which the user is interfacing; the provision of an improved method which employs standardized codes for directing Internet users to such content; the provision of such a method which employs International Classification of Diseases (ICD) codes or Current Procedural Terminology (CPT) codes; the provision of an improved Internet navigational system for providing health care information to a user; the provision of such a system employing standardized codes, such as ICD or CPT codes, to enable a user to retrieve content stored in a database.

Generally, a method of the present invention comprises storing content in a computer database, the content having a plurality of components. The method further comprises associating each of at least some of the content components with at least one of a plurality of codes (such as ICD or CPT codes) in a manner so that each of the plurality of codes employed has at least one of the content components associated therewith, and providing a retrieval system accessible by a user using the Internet. The retrieval system is adapted to retrieve the content components associated with any one of the codes upon receiving a signal sent by the user. The signal corresponds to said any one of the codes. The content components associated with said any one of codes are sent to the user upon receiving the signal.

Another aspect of the present invention is a method of supplying names of health care providers to Internet users. The method comprises storing the names of at least a plurality of health care providers in a computer database, and associating each of the names of the plurality of health care providers with at least one of a plurality codes (such as ICD or CPT codes). The names are associated with the codes in a manner so that each of the plurality of codes employed has at least one of the names associated therewith. The method further comprises providing a retrieval system accessible by a user using the Internet. The retrieval system is adapted to retrieve the stored names associated with any one of the codes upon receiving a signal from the user. The signal corresponds to said any one of the codes. The names associated with said any one of codes are sent to the user upon receiving the signal.

A further aspect of the present invention is an Internet navigational system. The navigational system comprises a computer database and a retrieval system. The computer database has content stored therein. The content has a plurality of components. Each of at least some of the content components are associated with at least one of a plurality of codes (such as ICD or CPT codes) in a manner such that each of the plurality of codes employed has at least one of the content components associated therewith. The retrieval system is accessible by a user using the Internet. The retrieval system is adapted to retrieve the content components associated with any one of the codes upon receiving a signal from the user. The signal corresponds to said any one of the codes.

Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
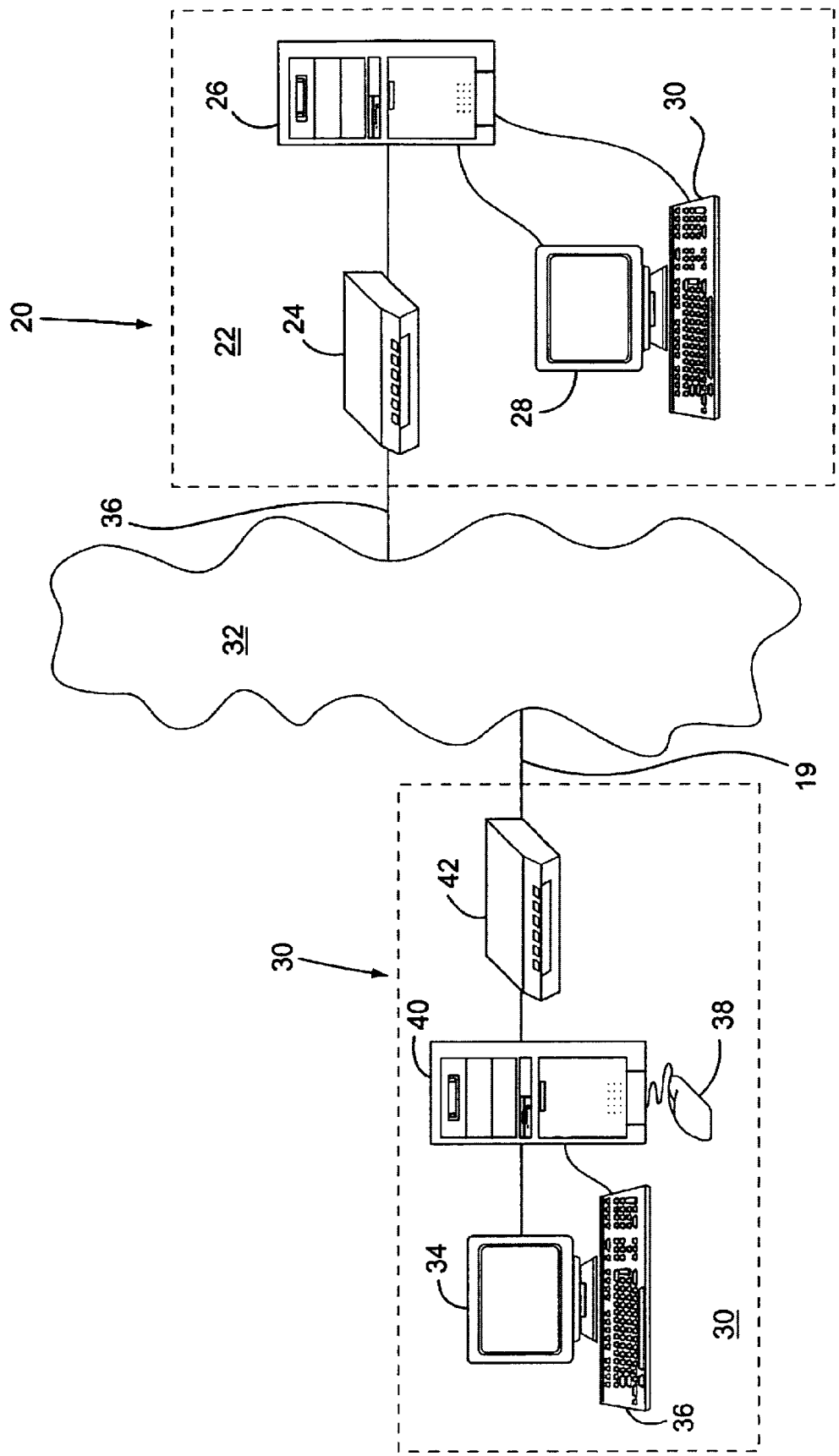
FIG. 1 is a simplified block diagram representing a computer system having an Internet navigational system of the present invention.

An Internet navigational system of the present invention is indicated generally in FIG. 1 by reference numeral 20. The Internet navigational system 20 comprises a server 22 for enabling an Internet user to retrieve information. The server 22 comprises a computer database and a retrieval system.

The retrieval system is preferably a database search engine (e.g., Broadvision, Verity, etc.). The server 22 is shown as a conventional computer system, rather generically comprising a network coupling device 24 of a suitable type, such as a high-speed analog or digital modem, a central processing unit (CPU) 26, a display 28 and a keyboard 30 for operator interaction. It should be understood that various means for entering data and observations other than keyboards are known. Such devices may include light pens, pointing devices such as a computer mouse, touch screens, or even microphones or video cameras or any other data input device, all of which can be configured to serve a function equivalent to a keyboard for purposes of this invention. The server 22 may, itself, be a computer network instead of the simple system shown in FIG. 1. In particular, server 22 may comprise one or more separate web servers and/or separate databases with extensive RAM and disk memory storage, or their functional equivalents. Although not shown in FIG. 1, portions of such a server network may be physically separate from one another, and these portions may communicate with each other over the Internet or over a separate network.

The navigational system 20 further includes at least one user terminal 30 coupled to the Internet 32 (or any other suitable communication network). The server 22 is also coupled to the Internet 32. In a commercially successful system, it is anticipated that there would be large numbers of user terminals of various different types in communication with the server 22. As is conventional at present, the user terminal 30 is shown as a conventional personal computer system including a display 34, a keyboard 36, a mouse 38, a system unit 40, and a modem 42. Usually, the modem couples to the Internet 20 via a data line 19 such as a cable or telephone line. Alternatively, the user terminal communicates with the Internet via wireless communication.

The server 22 is preferably functionally coupled to the Internet 32 and thus to terminals 32 via one or more dedicated, high-speed lines 34. The requirements for server 22 and high-speed lines 34 are dictated at least in part by the expected volume of data to be exchanged with users at user terminals and by the number of such user terminals and users that are expected to access the server.

Stated generally, the computer database has content stored therein and the content has a plurality of components. In the preferred embodiment, the content comprises a plurality of names of health care providers, such as physicians, chiropractors, nurses, psychologists, optometrists, etc. Consistent with the terminology used herein, each name constitutes a component of the plurality of names. Preferably, at least one standardized code (and more preferably at least one ICD or CPT code) is associated with each name.

The term "CPT codes" stands for Physician's Current Procedural Terminology codes and comprises a listing of descriptive terms and identifying codes for reporting medical services and procedures performed by physicians. The purpose of the terminology is to provide a uniform language for accurately describing medical, surgical, and diagnostic services. It provides an effective means for reliable nationwide communication among physicians, patients, and third parties. CPT descriptive terms and identifying codes currently serve a wide variety of important functions in the field of medical nomenclature. This system of terminology is the most widely accepted nomenclature for the reporting of physician procedures and services under government and private health insurance programs. CPT is also useful for administrative management purposes such as claims processing and for the development of guidelines for medical education and research by providing a useful basis for local, regional and national utilization comparisons. CPT codes are updated on an annual basis through the combined efforts of many individuals and organizations and are published through many outlets, including most medical organizations, providers, and the U.S. and most other governments. Most CPT codes are 5 digit codes, which can be modified by a number of suffixes.

As used herein, "ICD codes" means International Classification of Diseases codes. In 1948, the World Health Organization (WHO) published a statistical listing for tracking both morbidity and mortality. This listing, the International Classification of Diseases (ICD) led to the current text in international use today, the ICD ninth edition (ICD-9). This version precisely delineates the clinical picture of each patient, providing exact information beyond that needed for statistical groupings. ICD-9 codes are comprised of letters and numbers ranging from one letter and two numbers (generic diagnosis such as breast cancer) to one letter followed by 5 or more numbers. The extra digits constrict the diagnosis to become more specific.

A typical physician uses several CPT and ICD codes in his/her practice to chart and identify diagnoses or treatments of patient conditions. The specific CPT and ICD codes used may vary widely from physician to physician, even as to physicians having the same specialty. A primary reason for this is that the types of patients a physician might see vary from doctor to doctor. As between two plastic surgeons for example, one might specialize in breast augmentation and the other might specialize in treatment of burn victims. The former will use ICD and CPT codes concerning breast augmentation and the later will use ICD and CPT codes concerning diagnosis and treatment of burn victims.

As contemplated by the present invention, the ICD and CPT codes may be used to enable Internet users to find physicians. Perhaps stated more accurately, the ICD and CPT codes may be used to enable physicians to be located by potential patients which the physicians desire to treat. Rather than being listed by a relatively broad specialty, use of the ICD and CPT codes enables a physician to be listed for search-engine purposes by ailment, condition, and treatment options. A physician can choose to have his/her name be retrievable by any search within his/her area of practice, or can choose to have his/her name be retrievable only by searches related to certain ailments, conditions, or treatment options within his/her specialty. In other words, if a physician wants to expand his/her patient base for all areas within his/her specialty, all ICD and CPT codes within those areas can be associated with the physician's name. If a physician wants to expand his/her patient base for only certain areas of his/her specialty, the ICD and CPT codes concerning such certain areas can be associated with the physician's name. A physician can choose to have certain ICD and CPT codes associated with his/her name and choose to have other ICD and CPT codes not associated with his/her name.

Once a determination is made as to which ICD and CPT codes to identify with a physician, the physicians name and selected codes are entered into the database of the server 22. The retrieval system communicates with the database and is adapted to retrieve some or all of the names of the health care providers associated with any one of the ICD or CPT codes upon receiving a signal sent by a user. The signal corresponds to any one of the ICD or CPT codes.

In the present embodiment, the server 22 comprises components of a host computer system, generally indicated at 50, and the signal sent by a user comprises a signal sent by a client computer system 52 communicating with the host computer system. The host computer system 50 communicates with the client computer system 52 in a manner for providing on the client computer system an interface for the host computer system, and the host computer system is adapted to receive the signal via the interface. The interface may comprise a box, icon, or button on a screen of the client computer system 52. For example, the interface might be a box prompting the user to directly input an ICD or CPT code (e.g., by typing the code directly in the box) to initiate a search. This input is received by the retrieval system of the server 22. Upon receipt, the retrieval system retrieves from the database the names of the health care providers (and/or other content) associated with the ICD or CPT code, and conveys the search results to the client computer system 52.

Figure 2:
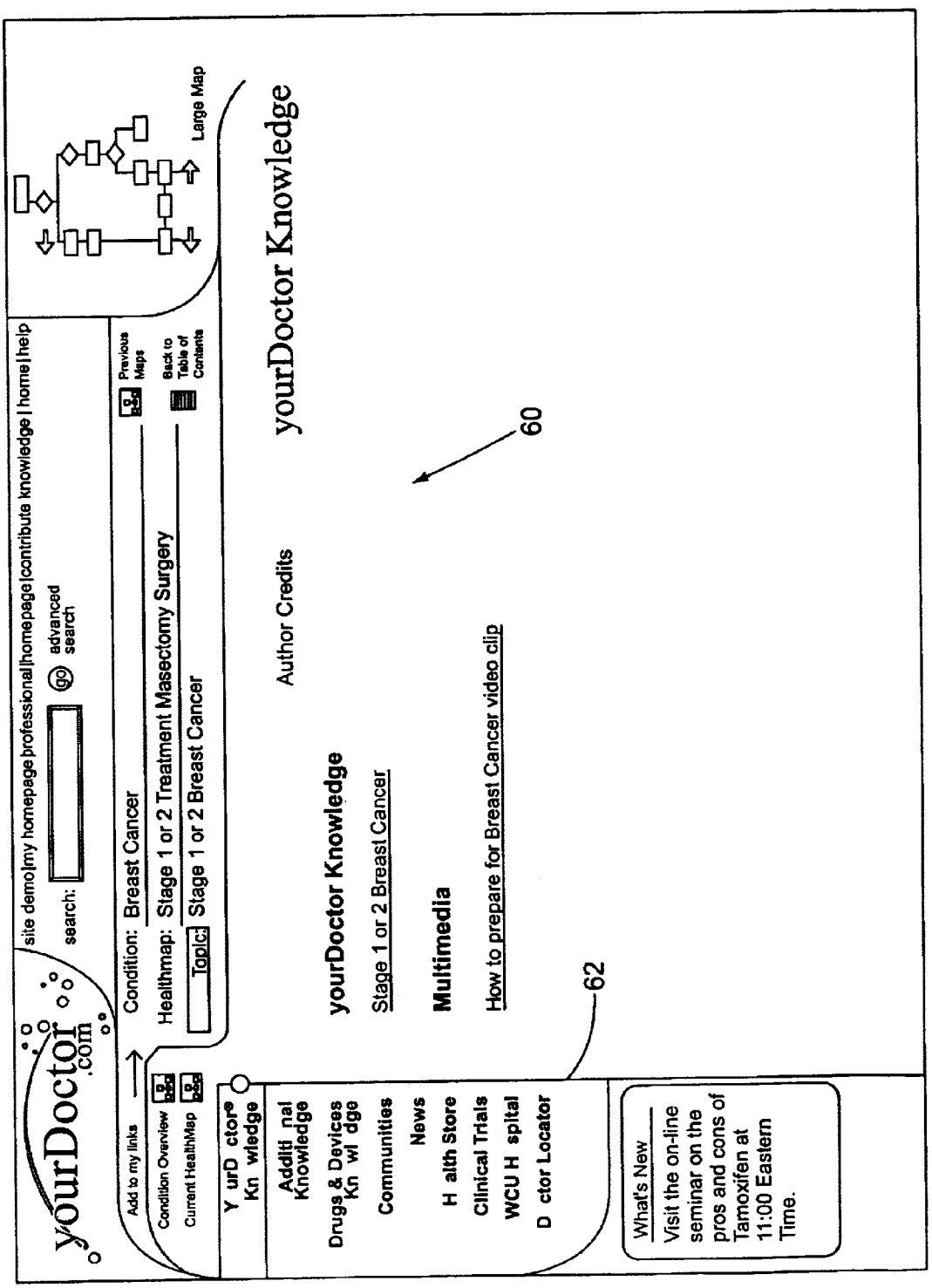
FIG. 2 is an exemplary interface having a series of buttons.

FIG. 2 shows an exemplary interface on a client screen, generally indicated at 60. Although the user may have the option of initiating a search by directly inputting an ICD or CPT code, it is expected that most Internet users will be unfamiliar with ICD and CPT codes. In one preferred mode of operation, the interface comprises a button or icon 62 appearing on the client screen 60 of the client computer system. Preferably, the icon 62 has a descriptive indicia (e.g., "Doctor Locator") to indicate its purpose. Preferably, the icon 62 appears on the client screen when the user is accessing a particular community or micro-community (e.g., a web page, chat room, resource tool, drug database, etc.) containing information about or somehow related to a particular ailment, condition, or treatment option. The user may be directed to select the button or icon 62 in order to retrieve a relevant list of health care providers. Because the web page or chat room relates to a particular ailment, condition, or treatment option, the system is adapted so that selection of the button or icon by the user sends to the host computer system 50 a signal associated with the ICD or CPT codes related to such ailment, condition, or treatment option. Another type of possible community is a health map as disclosed in commonly owned and co-pending U.S. patent application Ser. No. 09/547,781, filed Apr. 12, 2000 and titled A NAVAGATION SYSTEM AND METHOD FOR USING THE SAME (incorporated herein by reference). The maps and map nodes connect to specific databases, one of which may be a listing of ICD and CPT codes which are then associated with healthcare provider names. Also, map nodes may point directly to a database of healthcare provider names who want to be associated with that map and map node. Commonly owned and co-pending and pending U.S. patent application Ser. No. 09/425,779, filed Oct. 22, 1999, and titled APPARATUS AND METHOD FOR DIRECTING INTERNET USERS TO HEALTH CARE INFORMATION (hereby incorporated by reference) discloses use of ICD and CPT codes to obtain health care information. More particularly, such application envisions health care information being associated with ICD and CPT codes. The present invention complements the system described in such application by enabling a user to locate health care providers who specialize in the very subject matter that the user is then reading about.

In addition to providing the names of the health care providers associated with the ICD or CPT codes, it is to be understood that other information about the health care providers (e.g., the providers' addresses and/or telephone numbers, and perhaps some biographical information) may also typically be retrieved from the database and transmitted to the client computer system 52.

In practice, information about health care providers is stored in the database of the server 22. The information preferably includes basic information (e.g., name, address, telephone number) and specific information about the providers. The specific information includes the specific ICD and CPT codes with which any given provider wishes to be identified. Thus, Internet users retrieving health care information can also retrieve names and information of relevant health care providers.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A method comprising:

storing content in a computer database, the content having a plurality of components;

associating each of at least some of the content components with at least one of a plurality of ICD or CPT codes in a manner so that each of the plurality of ICD or CPT codes employed has at least one of the content components associated therewith;

providing a retrieval system accessible by a user using the Internet, the retrieval system being adapted to retrieve the content components associated with any one of the ICD or CPT codes upon receiving a signal sent by the user, the signal corresponding to said any one of the ICD or CPT codes, the retrieval system comprising a host computer system, the signal sent by the user comprising a signal sent by a client computer system communicating with the host computer system;

sending to the user the content components associated with said any one of the ICD or CPT codes upon receiving the signal;

the host computer system being adapted to retrieve descriptive healthcare information about a plurality of ailments and being adapted to send to the client computer system the descriptive information of any one of the plurality of ailments upon receiving from the client computer system a search query concerning said any one of the plurality of ailments;

associating the descriptive information of each of the plurality of ailments with a plurality of ICD or CPT codes;

sending the descriptive information of said any one of the plurality of ailments to the client computer system via the Internet, the sending of the descriptive information being initiated by the host computer system receiving from the client computer system the search query concerning said any one of the plurality of ailments.

2. A method as set forth in claim 1 wherein:

the descriptive information comprises one or more of the following: physiological aspects of the ailment, pathological aspects of the ailment, information as to whether the ailment is treatable, information about expected clinical course, and information about potential complications, the host computer system further being adapted to send to a client computer system communicating with the host computer system via the Internet the descriptive information of any one of the plurality of ailments upon receiving from the client computer system a search query concerning said any one of the plurality of ailments; and wherein the signal sent by the user is the search query concerning said any one of the plurality of ailments, whereby the signal corresponds to the ICD or CPT codes via the association of the descriptive information with the ICD or CPT codes.

3. A method as set forth in claim 2 wherein the plurality of content components comprises names of at least a plurality of health care providers.

4. A method as set forth in claim 3 wherein the step of associating each of at least some of the content components with at least one of a plurality of ICD or CPT codes comprises associating the names of the health care providers with the plurality of ICD or CPT codes in a manner such that each of the names of the health care providers is associated with at least one of the ICD or CPT codes.

5. A method as set forth in claim 4 wherein the ICD or CPT codes with which the name of each health care provider are associated are ICD or CPT codes chosen by each such health care provider.

6. A method as set forth in claim 4 wherein the step of associating the names of the health care providers with the plurality of ICD or CPT codes comprises associating each of at least some of the names with at least one of the ICD or CPT codes in a manner so that each of the plurality of ICD or CPT codes employed has at least one of the names associated therewith.

7. A method as set forth in claim 2 wherein the search query concerning said any one of the plurality of ailments comprises an ICD or CPT code.

8. A method as set forth in claim 2 wherein the host computer system communicates with the client computer system in a manner for providing on the client computer system an interface for the host computer system, the interface prompting a user to input a search query.

9. A method as set forth in claim 8 wherein the interface comprises a community, and wherein selection of the community by the user causes the search query to be sent to the host computer system.

10. A method as set forth in claim 8 wherein the interface comprises an icon on a community, and wherein selection of the icon by the user causes the search query to be sent to the host computer system.

11. A method as set forth in claim 10 wherein the community comprises a web page and wherein the icon is on the web page.

12. A method as set forth in claim 2 wherein the descriptive information comprises physiological aspects of the ailment.

13. A method as set forth in claim 2 wherein the descriptive information comprises pathological aspects of the ailment.

14. A method as set forth in claim 2 wherein the descriptive information comprises information as to whether the ailment is treatable.

15. A method as set forth in claim 2 wherein the descriptive information comprises potential complications.

16. An Internet navigational system comprising:
a computer database having content stored therein, the content having a plurality of content components, each of the content components being associated with at least one of a plurality of ICD or CPT codes in a manner such that each of the plurality of ICD or CPT codes employed has at least one of the content components associated therewith;
a retrieval system accessible by a user using the Internet, the retrieval system being adapted to retrieve the content components associated with the (CD or CPT codes upon receiving a signal from the user, the signal corresponding to said any one of the ICD or CPT codes, the retrieval system comprising at least a portion of a host computer system and wherein the host computer system is adapted to retrieve the content components associated with said any one of the ICD or CPT codes upon receiving the signal from a client computer system communicating with the host computer system;
the computer database comprising at least one computer database, the at least one computer database also having stored therein descriptive information about a plurality of ailments, the descriptive information of each of the plurality of ailments being associated with a plurality of ICD or CPT codes;
the host computer system being adapted to retrieve from the at least one computer database the descriptive information, the host computer system further being adapted and configured to send to a client computer system communicating with the host computer system via the Internet the descriptive information of any one of the plurality of ailments upon receiving from the client computer system a search query concerning said any one of the plurality of ailments, the host computer system further being adapted and configured to send to the client computer system via the Internet at least one of the content components based upon the association of the ICD or CPT codes such that the sent content components are associated with the ICD or CPT codes with which the sent descriptive information is associated.

17. An Internet navigational system as set forth in claim 16 wherein the descriptive information comprises one or more of the following: physiological aspects of the ailment, pathological aspects of the ailment, information as to whether the ailment is treatable, information about expected clinical course, and information about potential complications.

* * * * *